United States Patent
Waterworth et al.

(10) Patent No.: US 9,453,221 B2
(45) Date of Patent: Sep. 27, 2016

(54) ICAM-1 ANTISENSE FOR THE TREATMENT OF INFLAMMATION AND PAIN IN A RECTAL STUMP

(71) Applicant: ATLANTIC PHARMACEUTICALS (HOLDINGS) LTD, Saffron Walden, Essex (GB)

(72) Inventors: Toby Wilson Waterworth, Saffron Walden (GB); Huw Jones, Saffron Walden (GB)

(73) Assignee: ATLANTIC PHARMACEUTICALS (HOLDINGS) LTD, Saffron Walden, Essex (GB)

( * ) Notice: Subject to any disclaimer, the term of this patent is extended or adjusted under 35 U.S.C. 154(b) by 0 days.

(21) Appl. No.: 14/404,348

(22) PCT Filed: Jun. 3, 2013

(86) PCT No.: PCT/GB2013/051470
§ 371 (c)(1),
(2) Date: Nov. 26, 2014

(87) PCT Pub. No.: WO2013/179067
PCT Pub. Date: Dec. 5, 2013

(65) Prior Publication Data
US 2015/0337301 A1    Nov. 26, 2015

(30) Foreign Application Priority Data
Jun. 1, 2012   (GB) .................................. 1209895.0

(51) Int. Cl.
*A61K 48/00* (2006.01)
*C12N 15/113* (2010.01)
*A61K 31/7125* (2006.01)

(52) U.S. Cl.
CPC ......... *C12N 15/113* (2013.01); *A61K 31/7125* (2013.01)

(58) Field of Classification Search
None
See application file for complete search history.

(56) References Cited

U.S. PATENT DOCUMENTS

2009/0275631 A1* 11/2009 Wedel ................ C12N 15/1138 514/44 A
2011/0289608 A1* 11/2011 Schnell ................ A61K 31/713 800/9

OTHER PUBLICATIONS

Bennett CF, et al, An ICAM-1 antisense oligonucleotide prevents and reverses dextran sulfate sodium-induced colitis in mice, Feb. 1, 1997, pp. 988-1000, vol. 280, No. 2, Publisher: Journal of Pharmacology and Experimental Therapeutics. American Society for Pharmacology and Experimental Therapeutics, Published in: U.S.
D'Haens, et al, Early lesions of recurrent Chron's disease caused by infusion of intestinal contents in excluded ileum, Feb. 1, 1998, pp. 262-267, vol. 114, No. 2, Publisher: Gastroenterology, Elsevier, Published in Philadelphia, PA, U.S.
Edwards, et al, Diversion colitis—new light through old windows, Jan. 1, 1999, pp. 1-5, vol. 34, No. 1, Publisher: Histopathology.
Henry, et al, Evaluation of the toxicity of ISIS 2302, a phosphorothioate oligonucleotide. in a four-week study in cynomolgus monkeys, Jun. 1, 1997, pp. 145-155, vol. 120, No. 2, Publisher: Toxicology.
Miner JR P, et al, An Enema Formulation of Alicaforsen, an Antisense Inhibitor of Intercellular Adhesion Molecule-1, In the Treatment of Chronic, Unremitting Pouchitis, Jan. 1, 2004, pp. 281-286, vol. 19, Publisher: Alimentary Pharmacology & Therapeutics, Blackwell Scientific Publications Ltd ., Published in: Cambridge, GB.
Panes, et al, Leukocyte-endothelial cell interactions: Molecular mechanisms and implications in gastrointestinal disease, May 1, 1998, pp. 1066-1090, vol. 114, No. 5, Publisher: Gastroenterology, Elsevier, Published in Philadelphia, PA, U.S.
Rijcken, et al, ICAM-1 and VCAM-1 antisense oligonucleotides attenuate in vivo leucocyte adherence and inflammation in rat inflammatory bowel disease, Oct. 1, 2002, pp. 529-535, vol. 51, No. 4, Publisher: GUT.
Stucchi, et al, Stasis Predisposes Ileal Pouch Inflammation in a Rat Model of Ileal Pouch-Anal Anastomosis, Nov. 1, 2010, pp. 75-83, vol. 164, No. 1, Publisher: Journal of Surgical Research, Academic Press Inc., Published in: San Diego, CA, U.S.
Vainer B, Intercellular adhesion molecule-1 (ICAM-1) in ulcerative colitis: Presence, visualization, and significance, Aug. 1, 2005, pp. 313-327, vol. 54, No. 8, Publisher: Inflammmation Research; Official Journal of the International Association of Inflammation Societies the European Histamine Research Society, Published in: Birkhauser-Verlag, BA.
Yacyshyn, et al, A placebo-controlled trial of ICAM-1 antisense oligonucleotide in the treatment of Crohn's disease, Jun. 1, 1998, pp. 1133-1142, vol. 114, No. 6, Publisher: Gastroenterology, Elsevier, Published in: Philadelphia, PA, U.S.
Yacyshyn, et al, Double blind, placebo controlled trial of the remission inducing and steroid sparing properties of an ICAM-1 antisense oligodeoxynucleotide alicaforsen (ISIS 2302) in active steroid dependent Crohn's disease, Jul. 1, 2002, pp. 30-36, vol. 51, No. 1, Publisher: GUT, British Medical Association, Published in: London, UK.
International Search Report & Written Opinion, PCT/GB2013/051470, Aug. 29, 2013.

* cited by examiner

*Primary Examiner* — Kimberly Chong
(74) *Attorney, Agent, or Firm* — Karen S. Canady; canady + lortz LLP

(57) ABSTRACT

This invention relates to a composition comprising an antisense oligonucleotide that down-regulates intracellular adhesion molecule-1 (ICAM-1) for use in treating inflammation, pain and/or discharge in a rectal stump.

8 Claims, No Drawings

```
                      SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
gcccaagctg gcatccgtca                                               20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
cctgacggat gccagcttgg                                               20

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide

<400> SEQUENCE: 3
cccaagctgg catccgtca                                                19

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide

<400> SEQUENCE: 4
gcccaagctg gcatccgtc                                                19

<210> SEQ ID NO 5
<211> LENGTH: 13
<212> TYPE: DNA
<213> ORGANISM: Artificial Sequence
```

-continued

```
<220> FEATURE:
<223> OTHER INFORMATION: Oligonucleotide

<400> SEQUENCE: 5
gcccaagctg gca                                                        13
```

ICAM-1 ANTISENSE FOR THE TREATMENT OF INFLAMMATION AND PAIN IN A RECTAL STUMP

This invention relates to a composition comprising an antisense oligonucleotide that down-regulates intracellular adhesion molecule-1 (ICAM-1) for use in treating inflammation, pain and/or discharge in a rectal stump.

Patients suffering from disorders of the intestine may have to undergo surgery to remove a section of the intestine or the entire intestine. For example, this can be necessary in patients with colon cancer, diverticulitis and inflammatory bowel diseases such as ulcerative colitis or Crohn's disease.

In general, a surgeon will try and minimise the extent of the surgery and may leave the rectal stump intact. However, the rectal stump can become aggravated and inflamed, be very painful and/or discharge mucus and/or blood. It is believed a trigger is the absence of stools and a resulting change in the local environment and an absence of faecal bacterial flora.

In some cases, steroids, 5-aminosalicyclic acid (5-ASA) or immunomodulators are used to treat the aggravated rectal stump but a number of patients are resistant to these drugs and therefore an alternative approach for alleviating an aggravated rectal stump is required.

An ICAM-1 antisense oligonucleotide comprising the nucleic acid sequence of SEQ ID NO: 1 has previously been used to treat ulcerative colitis (UC) and pouchitis, both of which are conditions of a continuous intestine (not a blind ended intestine).

ICAM-1, a member of the immunoglobulin (Ig) superfamily, is an inducible transmembrane glycoprotein constitutively expressed at low levels on vascular endothelial cells and on a subset of leucocytes (Dustin et al., *J. Immunol,* 137:245-54, 1986; Rothlein et al, *J. Immunol.,* 137:1270-4, 1986; Simmons et al, *Nature,* 331:624-7, 1988). SEQ ID NO:1 is a 20-base phosphorothioate oligodeoxynucleotide designed to specifically hybridize to a sequence in the 3'-untranslated region of the human ICAM-1 mRNA. Studies strongly suggest that the ICAM-1 antisense oligonucleotide functions by specifically binding to the ICAM-1 mRNA resulting in cleavage of the mRNA by the enzyme RNaseH1 (Crooke, *Biochim. Biophys. Acta.,* 1489:31-44, 1999), one of an ubiquitous family of RNaseH nucleases.

It has been surprisingly found, by chance, that a composition comprising an oligonucleotide having a sequence comprising SEQ ID NO: 1 is extremely effective for reducing inflammation, pain and/or discharge in the rectal stump.

According to a first aspect of the invention, there is provided a composition comprising an oligonucleotide comprising the nucleic acid sequence of SEQ ID NO:1 and hydroxypropyl methylcellulose for use in treating inflammation, pain and/or discharge in a rectal stump.

SEQ ID NO:1 is as follows: 5'-gcccaagctg gcatccgtca-3'

In one embodiment, the composition comprises an oligonucleotide consisting of the nucleic acid sequence of SEQ ID NO:1.

The oligonucleotides in accordance with this invention preferably comprise from about 20 to about 80 nucleic acid base units. It is more preferred that such oligonucleotides comprise from about 20 to 50 nucleic acid base units, still more preferred to have from about 20 to 30 nucleic acid base units, and most preferred to have from about 20 to 22 nucleic acid base units. As will be appreciated, a nucleic acid base unit is a base-sugar combination suitably bound to an adjacent nucleic acid base unit through phosphodiester or other bonds. One skilled in the art will understand that about 20 to about 80 nucleic acid base units includes 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleobase units.

In a further embodiment, the composition comprises a fragment of SEQ ID NO:1, wherein the fragment is at least 8, 9, 10, 11, 12, 13, 14, 15, 16, 17, 18 or 19 nucleotides in length. The fragment can hybridise to a sequence in the 3'-untranslated region of the human ICAM-1 mRNA. The fragment can hybridise under moderate or stringent conditions with nucleotides 'cctgacg gatgccagct tgg' (SEQ ID NO:2). Fragments include 'cccaagctg gcatccgtca' (SEQ ID NO:3), 'gcccaagctg gcatccgtc' (SEQ ID NO:4) and 'gcccaagctg gca' (SEQ ID NO:5). "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

As herein defined, "Stringent conditions" or "highly stringency conditions", may be identified by those that: (1) employ low ionic strength and high temperature for washing, for example 0.015 M sodium chloride/0.0015 M sodium citrate/0.1% sodium dodecyl sulphate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 [mu]g/ml), 0.1% SDS, and 10% dextran sulphate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulphate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used herein, conditions of moderate or high stringency can be readily determined by those having ordinary skill in the art based on, for example, the length of the DNA. The basic conditions are set forth by Sambrook et al. Molecular Cloning: A Laboratory Manual, 2 ed. Vol. 1, pp. 1.101-104, Cold Spring Harbor Laboratory Press, (1989).

The oligonucleotide can be modified to comprise at least one phosphorothioate linkage. Phosphorothioate modification of the oligonucleotide, by substituting a sulfur molecule for a non-bridging oxygen molecule in each phosphodiester linkage, significantly increases exonuclease resistance relative to unmodified DNA and prolongs the drug half life (Geary et al., Anti-Cancer Drug Design, 12:383-94, 1997). Phosphorothioate oligonucleotides are only minimally antigenic, non-cytotoxic and well tolerated, and their pharmacokinetic and pharmacodynamic properties are well characterized (see e.g., Butler et al., Lab. Invest, 77:379-88, 1997; Mirabelli et al., Anti-Cancer Drug Des., 6:647-61, 1991).

In addition to phosphorothioate backbone modifications, a number of other possible backbone, sugar and other modifications are well known to those skilled in the art.

The rectal stump that benefits from being treated is an aggravated rectal stump. References to "aggravated rectal stump" herein mean a rectal stump that is inflamed, painful and/or discharges blood and/or mucous. Aggravation of the rectal stump is believed to be caused by an absence of stools, which results in an absence of faecal flora. The inflammation, pain and/or discharge can be symptoms of diversion colitis (also known as dysfunctional colitis). Accordingly, the composition can be for use in treating a subject with diversion colitis.

The composition for the use of the invention is particularly useful as the alternative is further surgery to remove the rectal stump, which is clearly very invasive for the patient and therefore traumatic, particularly as the patient will already have undergone significant surgery. Furthermore, there is a risk of death associated with the further surgery.

A rectal stump is formed when the rectum is closed and excluded from faecal transit after removal of the colon. The rectal stump can be a closed ended rectal stump or the upper end can exit to the lower part of an abdominal incision or as a mucous fistula in the left iliac fossa. In all cases, the rectum has been surgically severed from the gastro-intestinal tract.

In one embodiment, the composition is for use in treating a subject that does not suffer from colitis, particularly UC, and/or pouchitis. In a further embodiment, the subject has never suffered from colitis, particularly UC, and/or pouchitis.

The composition can be formulated for rectal administration. Compositions for rectal administration include solutions, such as enemas and suppositories, and emulsions or foams. Absorption promoting adjuvants can be included with the composition.

Formulations for the rectal delivery of pharmaceutical compositions are well known to those skilled in the art. The selection of a specific formulation is based on considerations well known to those skilled in the art. Detailed formulations are presented in U.S. Pat. Nos. 6,096,722 and 6,747,014 both incorporated herein by reference.

The composition may be for use in a patient that has a rectal stump of less than 25 cm, 20 cm, 15 cm, 10 cm, 9 cm, 8 cm, 7 cm, 6 cm or less than 5 cm.

The composition comprising an oligonucleotide comprising the nucleic acid sequence of SEQ ID NO:1 and hydroxypropyl methylcellulose may be administered alone but can also be combined with another pharmaceutical agent.

In a preferred embodiment, the subject is human.

The precise dose of the oligonucleotide will depend upon a number of factors, including the severity of the inflammation, pain and/or discharge. The composition is preferably administered to an individual in a "therapeutically effective amount", this being sufficient to show benefit to the individual.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

For example, in one embodiment, a suitable dose may be 60 ml/240 mg, 70 ml/240 mg, 80 ml/240 mg, 90 ml/240 mg, 100 ml/240 mg, 30 ml/120 mg, 60 ml/120 mg, 70 ml/120 mg, 80 ml/120 mg, 90 ml/120 mg, 100 ml/120 mg per dose, for example, per enema.

The composition may be administered once, twice, three or four times a day or periodically.

The composition can be administered for 3, 4, 5, 6, 7, 8 or more weeks. A peak response is achieved 8, 9, 10, 11, 12 weeks or more after the treatment commences. The patient can be in remission for 4-12, 6-12, 6-18 or more including 16-24 months after treatment.

The composition may be in respect of existing aggravation, inflammation, pain and/or discharge of the rectal stump or may be prophylactic (preventative treatment). Treatment may include curative, alleviation or prophylactic effects.

More specifically, treatment includes "therapeutic" and "prophylactic" and these types of treatment are to be considered in their broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition.

According to a second aspect of the invention, there is provided a method of treating inflammation, pain and/or discharge in the rectal stump in a subject, comprising administering a composition comprising an oligonucleotide comprising the nucleic acid sequence of SEQ ID NO:1 and hydroxypropyl methylcellulose to the subject.

In one embodiment, the subject is in need of such treatment or can benefit from such treatment.

A therapeutically effective amount of the oligonucleotide is administered to the subject.

The term "therapeutically effective amount" as used herein in the context of treating aggravated rectal stump means an amount capable of reducing inflammation, pain and/or discharge relative to the inflammation, pain and/or discharge experienced by the subject before the composition of the invention is administered.

The term 'treatment' is used herein to refer to any regimen that can benefit a human Preferred features for the second and subsequent aspects of the invention are as for the first aspect mutatis mutandis.

The invention will now be further described by way of reference to the following Example, which is provided for the purposes of illustration only and are not to be construed as being limiting on the invention.

EXAMPLE 1

This patient had a sub-total colectomy and ileostomy for active ulcerated colitis and underwent emergency surgery.

Surgery was performed as the patient was not responding to normal medical interventions for this condition.

Post Operative—patient presented with constant pain and a post rectal discharge of bleeding and mucus anything between 17-19 times over a period of 24 hours. He had rectal 5ASA to try and control the discharge. In July 2011 symptoms were worsening. The gastroenterologist was reluctant to use Aziathioprine as it had previously not been effective. The other option would have been use of Biologicals but the Gastroenterologist was reluctant to prescribe due to systemic effects.

He underwent proctoscopy on $19^{th}$ August and commenced a composition comprising SEQ ID NO:1 on $22^{nd}$ August.

He came back for review on the $4^{th}$ October. At that review he had reduced his post rectal discharge to blood only and to about 8-9 times a day. There was no pain and no mucus discharge.

The Specialist Nurse spoke to him on the 19 Jan. 2012 and he discharge had reduced to 3-6 times over a 24 hour period.

The patient feels that his quality of life has been significantly improved and that he has benefited greatly from the course of a composition comprising SEQ ID NO:1.

The invention claimed is:

1. A method of treating inflammation, pain and/or discharge in a rectal stump in a subject, comprising administering a composition comprising an oligonucleotide comprising the nucleic acid sequence of SEQ ID NO: 1 and hydroxypropyl methylcellulose to a subject having a rectal stump.

2. The method of claim 1, wherein the composition is formulated as an enema, suppository, emulsion or foam and the administering is for rectal administration.

3. The method of claim 1, wherein the rectal stump exhibits mucosal and/or blood discharge.

4. The method of claim 1, wherein the oligonucleotide comprises at least one phosphorothioate linkage.

5. The method of claim 1, wherein the rectal stump is 25 cm or less length.

6. The method of claim 1, wherein the inflammation, pain and/or discharge are symptoms of diversion colitis.

7. The method of claim 1, wherein the composition is administered in an amount effective to reduce inflammation, pain and/or discharge in a rectal stump.

8. The method of claim 7, wherein the inflammation, pain and/or discharge are symptoms of diversion colitis.

* * * * *